United States Patent [19]
Schramm et al.

[11] Patent Number: 5,935,864
[45] Date of Patent: *Aug. 10, 1999

[54] METHOD AND KIT FOR COLLECTING SAMPLES OF LIQUID SPECIMENS FOR ANALYTICAL TESTING

[75] Inventors: Willfried Schramm, Battle Ground; Anthony Burgess-Cassler, Vancouver, both of Wash.; Charles Haisley, Boulder, Colo.

[73] Assignee: Saliva Diagnostic Systems Inc., Vancouver, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/726,663

[22] Filed: Oct. 7, 1996

[51] Int. Cl.$^6$ .......................................... G01N 1/10
[52] U.S. Cl. ........................... 436/174; 436/169; 422/58; 422/61
[58] Field of Search ........................ 422/58, 61; 436/164, 436/167, 169, 174

[56] References Cited

U.S. PATENT DOCUMENTS

| | | |
|---|---|---|
| 4,235,601 | 11/1980 | Deutsch et al. . |
| 4,299,916 | 11/1981 | Litman et al. . |
| 4,409,988 | 10/1983 | Greenspan ............................. 128/759 |
| 4,418,702 | 12/1983 | Brown et al. . |
| 4,580,577 | 4/1986 | O'Brien et al. . |
| 4,635,488 | 1/1987 | Kremer . |
| 4,774,962 | 10/1988 | Hebel et al. . |
| 4,820,399 | 4/1989 | Senda et al. . |
| 4,900,663 | 2/1990 | Wie et al. . |
| 4,978,504 | 12/1990 | Nason ....................................... 422/61 |
| 4,999,285 | 3/1991 | Stiso . |
| 5,030,558 | 7/1991 | Litman et al. . |
| 5,039,607 | 8/1991 | Shold . |
| 5,056,521 | 10/1991 | Parsons et al. . |
| 5,141,850 | 8/1992 | Cole et al. . |

FOREIGN PATENT DOCUMENTS

| | | |
|---|---|---|
| 0187167 | 7/1986 | European Pat. Off. . |
| 0354704 | 7/1989 | European Pat. Off. . |
| WO8808534 | 11/1988 | WIPO . |
| WO9014163 | 11/1990 | WIPO . |
| WO9113355 | 9/1991 | WIPO . |
| WO9309431 | 5/1993 | WIPO . |
| WO9511621 | 5/1995 | WIPO . |

OTHER PUBLICATIONS

PCT Search Report Listing Above References Mar. 3, 1998.

*Primary Examiner*—Lyle A. Alexander
*Attorney, Agent, or Firm*—Stroock & Stroock & Lavan LLP

[57] ABSTRACT

A sample kit and a method for collecting a sample of a liquid specimen for analytical testing comprises a sample container and a reagent vial. The sample container includes an open end and a capillary end with a chamber disposed therebetween which includes analytical testing strips and the like within the chamber. The reagent vial is provided with a penetrable foil seal over an open end and a reagent therein for receipt of the capillary end of the sample container. The method for collecting a sample of a liquid specimen for analytical testing includes the steps of bringing the capillary end in contact with the liquid specimen to be analyzed and then penetrating the penetrable foil seal over the open end of the reagent vial wherein the sample container fits within the opening in the penetrable foil seal in an air-tight manner forcing the reagent within the reagent vial into the chamber in the sample container and thereby in contact with the analytical testing strips.

11 Claims, 2 Drawing Sheets

METHOD AND KIT FOR COLLECTING SAMPLES OF LIQUID SPECIMENS FOR ANALYTICAL TESTING

BACKGROUND OF THE INVENTION

This invention relates to a method for collecting, processing, and analyzing a liquid specimen in a self-contained system. More particularly, this invention relates to an is apparatus and method for collecting, processing, and analyzing liquid specimens in a self-contained system.

Chemical and biochemical analysis of liquids has been traditionally performed in specialized laboratories. However, the classical methods of analytical chemistry have been increasingly replaced by automated analyzers designed for the processing of well-defined specimens. These procedures are typically still conducted in highly specialized institutions by technicians trained in operating particular integrated instruments. In the recent past there has been an increasing trend to develop devices for the analysis of specimens in the field by non-trained personnel to address a specific analytical or diagnostic problem. In fully integrated devices sample collection, processing, and analysis are combined in such ways that they are non-obvious to the user but deliver a final non-coded readout. The degree of integration of all the procedures required for full analysis may vary in the descriptions of prior art.

Several devices and methods have been described to collect liquid specimens by means of fibrous or other absorbent materials for subsequent processing and analysis. Greenspan (U.S. Pat. No. 4,409,988) teaches an apparatus for collecting cultures where the specimen is taken up by the absorbent tip of a swab which is then transferred into a culture medium. In a similar fashion, Nason (U.S. Pat. No. 4,987,504) describes a specimen test unit for which the biological sample is also collected with a swab. For the collection of a specimen for medical diagnosis, Schluter (EP 0 382 905 A2) teaches the use of absorbent material for uptake of liquid and simultaneous separation of particulate matter. In yet another invention describing the collection of a body sample, Kremer (U.S. Pat. No. 4,635,488), a device with a nib containing porous material for absorption is taught. The focus of Zawydski et al's teaching (EP 0 354 704) is on a device for expressing liquid absorbed on a medical swab. A number of devices have been described for collecting oral fluid using an absorbent pad and extracting the fluid from the pad either with a barrel-piston arrangement (U.S. Pat. Nos. 4,418,702; 4,580,577; 4,774,962; 5,056,521) or by centrifugation (U.S. Pat. No. 4,774,962).

All of these applications teach the use of absorbent material to take up a liquid to be analyzed. However, these methods of specimen collection have distinct limitations in a number of applications. Some of these application include, for example:

1. Absorption of molecules or components by the large surface area of absorbent materials if these molecules or components are to be quantitatively analyzed or if they are in a low concentration so that qualitative analysis is impaired (i.e., interference of non-specific binding).

2. Destruction or modification of molecules or components from the liquid to be analyzed by the absorbent materials (e.g., hemolysis of red blood cells in whole blood specimens, catalytic reactions, chemical reactions, etc.)

3. Inaccurate volume uptake, particularly for small volumes (e.g. microliters) and for viscous liquids (e.g. whole blood).

4. Adjustment of hydrophilicity/lipophilicity between the absorbent material and the liquid to be taken up (i.e., non-wettability).

5. Limited capability for expression/desorption of liquid taken up by absorbent materials, particularly for highly viscous liquids (i.e., incomplete recovery of liquid).

SUMMARY OF THE INVENTION

An object of the present invention is to provide a method for collecting liquid specimens for analytical testing.

Another object of the present invention is to provide a method for collecting liquid specimens utilizing sample containers with open capillaries for the collection of liquid specimens for further analyses.

An even further object of the present invention is to provide a method for analyzing bodily fluids in a self-contained unit.

Also an object of the present invention is to provide a self-contained analyzing kit for the testing of liquid specimens, particularly bodily fluids.

More particularly, the present invention provides a method for collecting samples of a liquid specimen for analytical testing comprising the steps of: bringing into contact with a liquid specimen an open capillary end of a sample container and forcing said specimen into said capillary, the sample container having an open top with a chamber disposed between said capillary end and said open top, said chamber including means therein for analytical testing; placing said capillary end into a vial containing an analytical testing reagent; mixing said liquid specimen with said reagent; and, forcing said liquid specimen and said reagent through said capillary end into the chamber whereby the liquid specimen and said reagent are analyzed.

Even more particularly, the present invention provides a self-contained unit for collecting and analyzing samples of liquid specimen including a sample container having an open capillary end and an open top with a chamber disposed therebetween, said chamber including means therein for analytical testing; and, a vial having a sealed top end, said top end being of preselected size to receive the lower end of said sample container in a substantially air tight arrangement upon being penetrated by said capillary end.

In the use of the term "capillary", such term will be used in the description of this invention in a broad definition insofar as the shape of the capillary may vary. The capillary will be defined as the mechanism of taking up liquid and the filling of a suitable open space as a result of surface tension between the liquid and the surface of the container.

Accordingly, other objects, features and advantages of the present invention will be apparent by reference to the following description of preferred embodiments, drawings and claims.

BRIEF DESCRIPTION OF THE DRAWINGS

A better understanding of the present invention may be obtained from the following detailed description of the preferred embodiments described in connection with the accompanying drawings wherein.

DETAILED DESCRIPTION OF THE PREFERRED EMBODIMENTS

Figure 1:
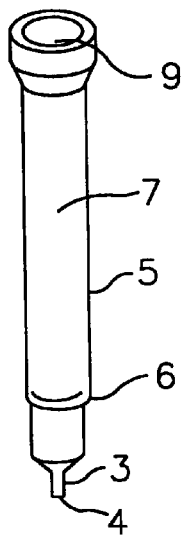
FIG. 1 is a perspective view of one preferred sample container of the present invention.
Figure 6A:
FIG. 6a is a perspective view of a capillary end of the sample container of FIG. 1.
Figure 6B:
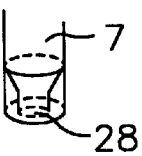
FIG. 6b is a capillary end of another preferred sample container.
Figure 6C:
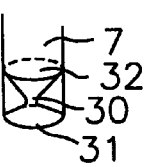
FIG. 6c is a capillary end of even another preferred sample container of the present invention.

As shown in FIG. 1, a sample container 5 is provided with a capillary 3 having an open capillary end 4 and an open top 9 with a chamber 7 disposed therebetween. Variations in the shape of the container 5, the position of the open top 9, as well as the size and shape of the capillary 3 may vary depending upon the particular liquid specimens to be analyzed. For example, with the collection of a small volume, that is from 1 to 5 microliters, a narrow capillary 3, as best shown in FIG. 6a, with a relatively small capillary opening 4 is advantageous. However, for the collection of larger volumes, that is for 10 to 25 microliters of, for example, whole blood, a capillary with a larger opening 28, as shown in FIG. 6b, is preferred. Moreover, as shown in FIG. 6b, the larger opening 28 may be built into the chamber 7 without forming a separate part therefrom. Also, for use in other applications, such as the collection of liquids with high surface tensions on certain solid surfaces which includes, for example, oils or syrups, or the like, a specially shaped capillary, such as shown in FIG. 6c, may be appropriate. As shown in FIG. 6c an indentation or capillary passageway 30 within the chamber 7 may be used to facilitate the identification of proper filling wherein the filling of the narrow passage of the indentation 30 can be easily seen by the user. Moreover, extension into a funnel-like shape 32 filling beyond the narrow passage indentation 30 takes place only reluctantly, depending upon the surface tension of the liquid, and a volume of the liquid with a high surface tension can be collected with relatively high accuracy. For other applications, a larger volume of liquid is required for analyses. In this instance, a wider opening of the capillary such as 28 and 31 in FIGS. 6b and 6c is desirable. Only if the entire opening is covered with liquid, liquid will rise into the capillary thus discouraging the collection of an insufficient volume of blood. A conically shaped capillary, as shown in FIG. 6c provides the advantage that the filling of the capillary with a pre-defined volume can be readily seen.

Figure 2:
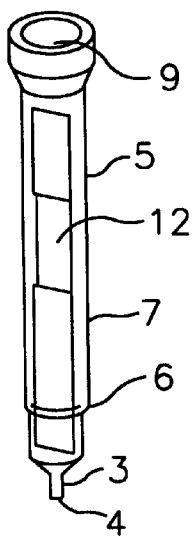
FIG. 2 is a perspective view of the sample container of FIG. 1 with a test strip for analysis inserted therein.

As best shown in FIG. 2, the chamber 7 accommodates a test strip 12 for analysis of the bodily fluid to be analyzed. These test strips are well known in the prior art. These include test strips containing immunochemical reagents and designed not to require handling for performance as set forth in U.S. Pat. No. 4,900,663; U.S. Pat. No. 5,030,558; U.S. Pat. No. 5,039,607 and U.S. Pat. No. 4,999,285. Moreover, analysis may include non-immunochemical techniques for analyte detection using inorganic chemical reactions such as those described in the scientific literature, such as, Fiegl, Frit, *Spot Tests in Inorganic Analysis, 6th Edition*, Elsevier Publishing Co., New York, 1972; organic chemical reactions as taught in Fiegl, Frit, *Spot Tests in Organic Analysis, 7th Edition*, Elsevier Publishing Co., New York, 1966; chelating reactions as taught in Braibanti, A., Editor, *Bioenergetics and Thermodynamics: Model Systems—Synthetic and Natural Chelates and Macrocycles as Models for Biological and Pharmaceutical Studies*, D. Reidel Publishing Co., Boston 1980; colorimetric reactions as taught in Snell F. and Snell C., *Colorimetric Methods of Analysis*, Vols. 1–4AAA, Van Nostrand Reinhold Co., New York, 1967–74; and enzyme electrodes as taught by Senda et al., U.S. Pat. No, 4,820,399.

Figure 3:
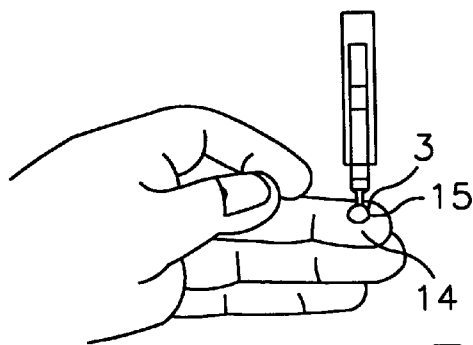
FIG. 3 is a perspective view of the sample container of FIG. 1 shown in contact with a liquid specimen source.
Figure 3A:
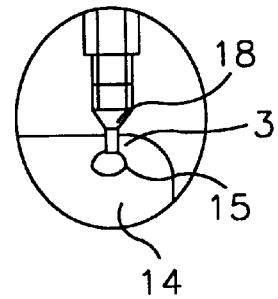
FIG. 3a is an enlarged side view of the capillary end of the sample container in contact with the liquid specimen source of FIG. 3.

As shown in FIG. 3, the capillary 3 of the sample container 5 is brought into contact with a liquid by touching the liquid with the capillary open end 4. The liquid specimen, for example, a bodily fluid to be analyzed is shown as a drop of blood identified by the number 15 which is obtained by pricking a finger tip 14 with a sharp object, such as a medical lancet. The dimensions of the capillary 3 and the surface tension of the liquid determine the extension of the upper meniscus 18 in the capillary, as shown in FIG. 3a, and, consequently, the volume of the liquid picked up.

Figure 4:
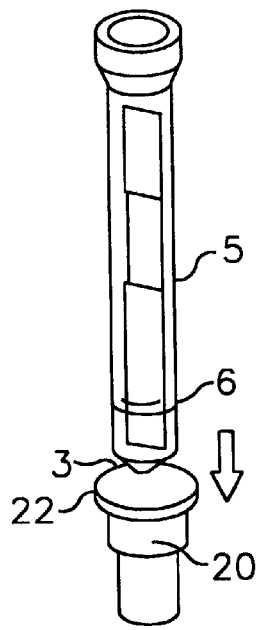
FIG. 4 is a perspective view of a preferred sample collecting kit of the present invention.
Figure 5:
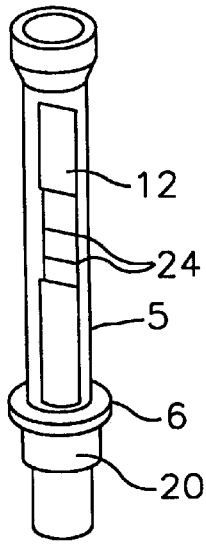
FIG. 5 is a perspective view of the sample container and reagent vial of FIG. 4 with the capillary end of the sample container being inserted into the reagent vial.

As shown in FIGS. 4 and 5, the liquid in the capillary 3 is diluted and flushed into the chamber 7 of the sample container 5 with another solvent by forcing the capillary through a septum 22 and subsequently into a solvent (buffer) vial 20. The solvent may be an aqueous or non-aqueous medium, for example, such as a buffer solution. The buffer solution may be contained in the buffer vial 20 that is sealed with a penetrable foil, as the septum 22. The sample container 5 is provided with an inwardly extending portion 6 that fits air-tight into the vial 20 thus inducing a pressure that flushes the content of the vial 20 through the capillary 3. The resulting liquid/buffer mixture enters the chamber 7 where it can be analyzed. For example, in using immunochromatographic test strip 12 for analyzing the liquid/buffer mixture as indicated by lines 24 in FIG. 5, an indication as a control and reaction indicator can be generated such as those described in U.S. Pat. Nos. 4,299,916; 4,235,601; and, 5,141,850.

Figure 7:
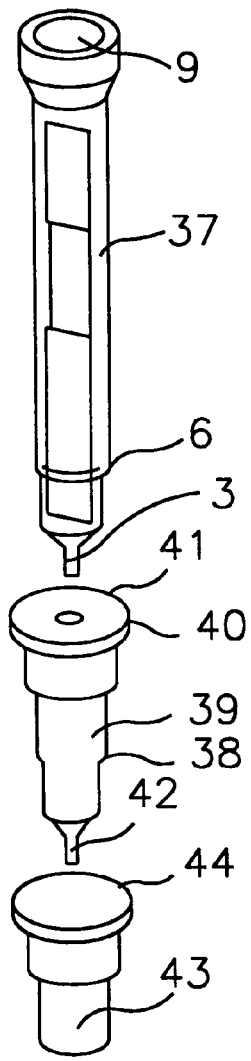
FIG. 7 is a perspective view of another preferred sample collecting kit of the present invention.
Figure 8:
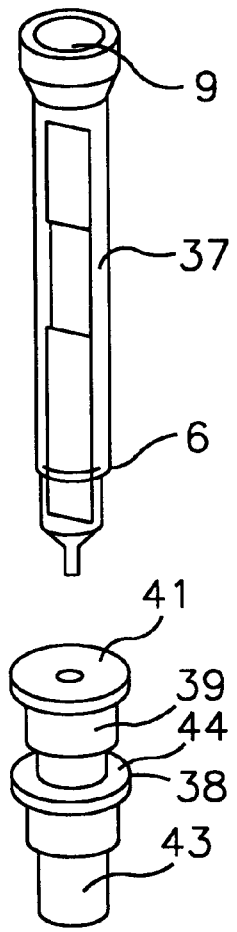
FIG. 8 is a perspective view of the sample kit of FIG. 7 showing two reagent vials in contacting relation; and, FIG. 9 is a perspective view of the kit of FIG. 7 with the sample container in contacting relation with the two reagent vials.
Figure 9:
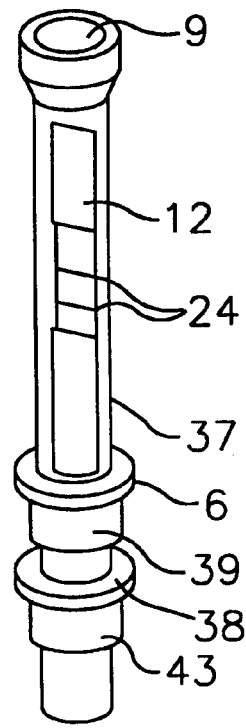

In another embodiment of the present invention, as shown in FIGS. 7–9, a sample kit may be provided with more than one capillary to perform certain analytical and processing procedures. One preferred sample kit as shown in FIG. 7 consists of three members, a sample container 37, an auxiliary container 39 and a vial 43 containing a liquid, such as, for example, a buffer solution. The auxiliary container 39 is provided with a second capillary end 42 and a seal 40 with a vent 41 therein. The auxiliary container 39 is also provided with an indented portion, identified by the numeral 38, for an air tight seal with the vial 43 upon contact between the auxiliary container 39 and the vial 43.

In FIG. 8 is shown the first step in the use of the sample test kit of FIG. 7 wherein the capillary 42 of the auxiliary container 39 is brought into contact with the solution in the vial 43 by inserting of the capillary 42 through a penetrable foil 44. The capillary 42 fills with liquid if the seal 40 has a vent 41, as shown, relieving the pressure therein. Alternatively, if it is advisable that the seal 40 does not have a vent to prevent contact of the contents within the vial 43, the seal 40 may be removed before the capillary 42 is filled with the solution from the vial 43. Also, the auxiliary container 39 may contain dried reagents therein for further reactions. As shown in FIG. 8, the auxiliary container 39 is pressed into the vial 43 with the contents of a liquid specimen from the capillary 42 being pressed into the interior of the auxiliary container 39 and mixes with the liquid content of the vial 43. If the auxiliary container 39 contains dried or solid reagent, for example, these are reconstituted with the liquid content of vial 43 and a reaction is initiated between the liquid content, the liquid specimen from the capillary 42 of the auxiliary container 39 and the dry reagents in the auxiliary container 39.

As shown in FIG. 9, the next step in taking a sample with the sample kit as shown in FIG. 7, a second liquid can be sampled with the capillary 3 of the sample container 37. This sample container 37 is subsequently pressed into the combined containers 39 and 43, thus mixing the combined liquids in auxiliary container 39 with the second liquid in the capillary 3. This combined mixture can then be analyzed by means of analytical devices contained in the sample container 37, such as the immunochromatographic test strips 12 which develop indicator lines 24. It is recognized that in the embodiment described in FIGS. 7–9 either of the liquids contained in capillary 3 or 42 may be the liquid specimen, such as a bodily fluid, to be tested and the other liquid may be an additional reagent that is required for the analytical reaction in a predefined volume. In a variation of this embodiment, both of the liquids in the capillaries 3 and 42 may be evaluated together, for example, for compatibility testing. In even another variation of this embodiment, the capillary 3 of the sample container 37 may not be filled at all, for example, if a two-step reaction is required for analyses.

It is realized that other variations and modifications of the preferred embodiment are possible without departing from the scope and spirit of the present invention. And, it is not intended that the aforementioned discussion in any way limits the scope of the present invention, as set forth in the appended claims.

What is claimed is:

1. A method for collecting a sample of a liquid specimen for analytical testing consisting essentially of the steps of:

bringing into contact with a liquid specimen to be tested an open capillary end of a sample container, and drawing said specimen into said capillary end, said sample container having an open top with a chamber disposed between said capillary end and said open top, said chamber including means therein for analytical testing;

placing said capillary end into a vial containing an analytical testing reagent and forcing said reagent into said open end;

mixing said liquid specimen with said reagent in said capillary; and drawing said liquid specimen and said reagent through said capillary end into said chamber whereby said liquid specimen and said reagent contact said means for analytical testing and said liquid specimen is analyzed.

2. The method of claim 1, said liquid specimen being bodily fluids.

3. The method of claim 1, said placing said capillary into a vial including penetrating a penetrable foil seal on said vial, said sample container fitting within said vial in an air-tight arrangement.

4. The method of claim 3, said sample container having an inwardly extending portion, said inwardly extending portion fitting within said seal at said penetrating.

5. The method of claim 1 wherein said vial contains a penetrable foil seal over an opening in a top thereof and said sample container includes means to provide an air tight seal when said capillary is received in said penetrable foil.

6. A sample collecting kit consisting essentially of a sample container having a capillary with an open end and an open top with a chamber disposed there between, said chamber including means therein for analytical testing; and, a vial having an open end for receiving said capillary therein, said vial including an analytical testing reagent therein, said open end including means for forcing the reagent into the capillary and means to mix liquid with the reagent.

7. The sample kit of claim 6, said vial having a penetrable foil over said open end of said vial.

8. The sample kit of claim 7, said sample container including means to form an air tight seal with said penetrable foil upon receipt of said capillary.

9. The sample kit of claim 8, said sample container having an inwardly extending portion, said inwardly extending portion engageable with an opening in said penetrable foil to form an air-tight seal between said sample container and said vial.

10. The sample kit of claim 6, said chamber having a capillary disposed therein.

11. The sample kit of claim 6, said chamber having a funnel-shaped opening in a lower end, said funnel-shaped opening opening outwards from said chamber and opposite said opening a capillary extending inwardly into said chamber.

* * * * *